United States Patent [19]

Dierassi et al.

[11] 4,330,438

[45] May 18, 1982

[54] POWDERED SHAMPOO CONCENTRATE

[75] Inventors: David Dierassi, West Orange; David Murray, Bloomfield, both of N.J.

[73] Assignee: Hoffmann-La Roche Inc., Nutley, N.J.

[21] Appl. No.: 220,587

[22] Filed: Dec. 29, 1980

[51] Int. Cl.$^3$ .................... C11D 17/06; C11D 1/14
[52] U.S. Cl. ........................... 252/552; 252/174.23; 252/550; 252/555; 252/DIG. 1; 252/DIG. 2; 252/DIG. 13; 252/DIG. 14; 424/70
[58] Field of Search .................. 252/174.23, 552, 550, 252/555, DIG. 1, DIG. 2, DIG. 13, DIG. 14; 424/70, 78

[56] References Cited

U.S. PATENT DOCUMENTS

| | | | |
|---|---|---|---|
| 2,307,047 | 1/1943 | Katzman et al. | 252/354 |
| 3,723,408 | 3/1973 | Nordgren et al. | 424/70 X |
| 3,776,861 | 12/1973 | Mausner et al. | 252/545 |
| 3,870,660 | 3/1975 | Paviak | 252/545 |
| 4,061,602 | 12/1977 | Oberstar et al. | 252/547 |
| 4,220,548 | 9/1980 | Hashimoto et al. | 252/106 |
| 4,253,993 | 3/1981 | Ramsey et al. | 252/548 |
| 4,260,528 | 4/1981 | Fox et al. | 252/525 |

FOREIGN PATENT DOCUMENTS 48-17528  5/1973  Japan.

*Primary Examiner*—P. E. Willis, Jr.
*Attorney, Agent, or Firm*—Jon S. Saxe; George M. Gould; John J. Maitner

[57] ABSTRACT

A unique powder shampoo concentrate is disclosed comprising a mixture of an anionic surfactant and a nonionic derivative of a polygalactomannan gum together with conventional shampoo ingredients, which upon dilution with water, rapidly forms a viscous, rich lathering shampoo with superior cleansing and conditioning properties.

8 Claims, No Drawings

POWDERED SHAMPOO CONCENTRATE

BACKGROUND OF THE INVENTION

It is known that when conventional liquid shampoo concentrates are diluted with water, the resulting shampoos lack either the desired viscosity or the ability to cleanse the hair properly. In addition, the hair is often dull, tangled and difficult to comb.

There is a need for a powder shampoo concentrate for professional use which, on addition of water, rapidly forms a rich, viscous, ready to use shampoo with desired viscosity, foaming, cleansing, rinseability and conditioning characteristics. A powder shampoo concentrate also offers considerable savings in the cost of packaging, transportation and storage where large volume use is a factor.

In accordance with the present invention, a powder shampoo concentrate is provided which possesses not only superior cleansing properties but also provides conditioning properties of a fine ready to use retail shampoo.

SUMMARY OF THE INVENTION

This invention relates to powder shampoo concentrates which comprise a combination of an anionic surfactant and a nonionic derivative of a polygalactomannan gum together with conventional shampoo ingredients. These concentrates readily form liquid shampoos, when admixed with water, which are viscous and have satisfactory foaming and rinsability properties. The shampoos prepared from the powder concentrates of this invention cleanse, impart luster, detangle and improve combability of human hair.

DESCRIPTION OF THE INVENTION

The present invention relates to powder shampoo concentrates for cleansing and conditioning hair comprising:

(a) From about 50 to 75 parts by weight alkali metal or ammonium salt of an alpha olefin sulfonate containing from 12-18 carbon atoms;

(b) from 18 to 30 parts by weight of a nonionic hydroxypropyl derivative of a polygalactomannan gum having from 0.35 to 0.90 moles of substitution.

The unique powder shampoo concentrate of the present invention, upon dilution with water, affords a superior rich lather, cleansing shampoo which, unexpectedly, provides conditioning properties. By "conditioning" is meant the deposition of a palpable film on the hair during shampooing. The film deposited on the hair from shampoos prepared from the novel powder concentrates of this invention acts to impart combability and manageability thereto. The film reduces tangling of the hair by reducing wet comb drag, reduces static charge and also imparts a softness and luster to the hair.

The present invention is concerned with the discovery that a unique combination of an anionic surfactant and a nonionic derivative of a polygalactomannan gum can be formulated into a powder concentrate which upon dilution with water rapidly forms a viscous, rich lathering shampoo possessing superior cleansing ability and simultaneously deposits a film on the hair. This film, which acts to condition the hair, adheres sufficiently well thereto to remain after the hair is rinsed off with water.

It has been found that the ingredients utilized in preparing the shampoo concentrate of this invention are characterized as being free flowing powders which possess good water solubility, i.e. they must be soluble in cold water in approximately one minute.

Anionic surfactants which are useful in the practice of the present invention include alpha olefin sulfonates having from 12 to 18 carbon atoms. They are used in the form of water-soluble salts, for example, the sodium, potassium and ammonium salts. A preferred material is sodium alpha olefin sulfonate having 14 to 16 carbon atoms which is commercially available. The amount of alpha olefin sulfonate necessary to obtain the desired effect is from about 50 to 75 parts by weight, and preferably from about 50–60 parts by weight.

The polygalactomannan gums utilized in this invention are nonionic derivatives, particularly hydroxyalkyl derivatives. Polygalactomannan gums are high molecular weight carbohydrate polymers or polysaccharides and contain as the basic unit two mannose units with a glycosidic linkage and a galactose unit attached to one of the hydroxyl groups of the mannose units. On average, each of the sugar units has three available hydroxyl sites. The hydroxyl groups of the polygalactomannan are reacted with alkylene oxide, e.g. ethylene oxide, propylene oxide, and the like, to produce the nonionic derivatives of polygalactomannan used in the present invention. Various derivatives can be obtained depending on the alkylene oxide used and the moles of substitution (M.S.). Useful materials for this invention are nonionic hydroxypropyl derivatives of polygalactomannan having from about 0.35 to 0.90 moles of substitution, preferably hydroxypropyl derivatives having preferably 0.35 to 0.60 moles of substitution. These materials are commercially available from Stein Hall and Co., Inc., New York under the tradename Jaguar HP-8, HP11 and HP-60. The amount of polygalactomannan gum necessary to accomplish the desired effect is from about 18 to 30 parts by weight.

The powder shampoo concentrates made in accordance with the present invention can contain other conventional shampoo ingredients. Included in such ingredients are: auxilary conditioning agents, for example, pathenol, pantyl, phytantriol, hydrolyzed animal protein, hydrolyzed milk protein; moisturizing agents, for example, squalene, mineral oil, 2-pyrrolidone-5-carboxyl acid; pH adjusters, for example citric acid, tartaric acid, fumaric acid; preservatives, for example, methyl paraben, propyl paraben and imidazolidinyl urea; protein derivatives, for example, hydrolyzed animal protein; sequestring ingredients, for example, disodium EDTA, Trisodium EDTA; anticaking agents, for example, hydrated silica; as well as conventional fragrances and colorants. When the foregoing conventional shampoo ingredients are present in the powder concentrate, they range from 0.4 to 25 parts by weight.

It has been found useful to add an alkyl sulfate to the powder concentrates of the present invention to enhance the foaming properties of the final shampoo. Alkyl sulfates having from 12 to 20 carbon atoms are used in the form of water-soluble salts, for example the sodium, potassium and ammonium salts. A specific example is sodium lauryl sulfate. The amount of alkyl sulfate utilized in the powder concentrate is from about 8 to 25 parts by weight.

The compositions of the invention are prepared, generally, by mixing the various ingredients in a suitable container to afford an intimate powder mixture of said ingredients. The mixture may be passed through a sieve to obtain a uniform particle size range for the powder concentrate. The mixing procedure can be accomplished by any suitable mixing or blending apparatus for powder materials.

Shampoo solutions are prepared from the powder concentrates described herein by diluting 1 part by weight of powder concentrate with from 38 to 40 parts by weight of water, and preferably 1 part by weight of powder concentrate with 39 parts by weight of water. The pH of shampoo compositions when diluted with tap water at a ratio of 1:39 is between about 5.5 to 7.5.

The following examples illustrate the invention:

EXAMPLE 1

| Ingredient | Parts by Weight |
|---|---|
| Sodium olefin sulfonate C14–C16 | 74.00 |
| Hydroxypropyl guar gum nonionic* | 22.80 |
| Citric Acid | 0.15 |
| Hydrolyzed animal protein | 2.00 |
| Perfume | 1.00 |
| Colorants | .05 |

*Jaguar HP-60, Stein, Hall and Co. Inc.

The composition is prepared by weighing all of the ingredients into a suitable mixer and mixing 2 minutes. The mixture is passed through a 30 mesh screen.

A shampoo solution is prepared by diluting 1 part by weight of the powder-mix with 39 parts by weight of tap water and stirring for 1 minute.

Clean hair tresses are shampooed with the above compositions. The results of this test indicate that the tresses are low in friction during wet combing, feel smooth and look shiny and lustrous when dry.

EXAMPLE 2

This Example illustrates the effect of substituting an anionic hydroxypropyl guar gum for the nonionic derivative.

| Ingredient | Parts by Weight A | B |
|---|---|---|
| Sodium C14–C16 Olefin Sulfonate | 56.800 | 56.800 |
| Sodium Lauryl Sulfate | 20.000 | 20.000 |
| Hydroxypropyl Guar Gum Non-ionic* | 20.000 | — |
| Hydroxypropyl Guar Gum Anionic** | — | 20.000 |
| Citric Acid | 0.150 | 0.150 |
| Hydrolyzed Animal Protein | 2.000 | 2.000 |
| Perfume | 1.000 | 1.000 |
| Colorants | 0.050 | 0.050 |

*Jaguar HP-60, Stein, Hall and Co., Inc.
**Jaguar CMHP, Stein, Hall and Co., Inc.

The compositions are prepared by weighing all of the ingredients into a suitable mixer and mixing for two minutes. The mixture is passed through a 30 mesh screen.

A shampoo solution is prepared by diluting 1 part by weight of the powder mix with 39 parts by weight of tap water and stirring for 1 minute.

Clean hair tresses are shampooed with compositions A and B. The tresses washed with composition A are low in friction during wet combing, feel smooth and look shiny and lustrous when dry. The tresses shampooed with composition B do not exhibit these characteristics.

EXAMPLE 3

This Example illustrates the effect of the amount of hydroxypropyl guar gum nonionic in the powder shampoo concentrates.

| Ingredients | Parts by weight A | B | C | D | E |
|---|---|---|---|---|---|
| Sodium C14–C16 Olefin Sulfonate | 61.80 | 66.80 | 66.80 | 66.80 | 58.80 |
| Sodium Lauryl Sulfate | 35.00 | 15.00 | 15.00 | 10.00 | 8.00 |
| Hydroxypropyl Guar Gum Non-ionic | — | 15.00 | 20.00 | 25.00 | 30.00 |
| Citric Acid | 0.15 | 0.15 | 0.15 | 0.15 | 0.15 |
| Hydrolyzed Animal Protein | 2.00 | 2.00 | 2.00 | 2.00 | 2.00 |
| Perfume | 1.00 | 1.00 | 1.00 | 1.00 | 1.00 |
| Colorants | 0.05 | 0.05 | 0.05 | 0.05 | 0.05 |

The compositions are prepared by weighing all of the ingredients into a suitable mixer and mixing for 2 minutes. The mixture is passed through a 30 mesh screen.

A shampoo solution is prepared by diluting 1 part by weight of the powder mix with 39 parts by weight of tap water and stirring for 1 minute.

Clean hair tresses are shampooed with compositions A–E. The tresses washed with composition C, D and E are low in friction during wet combing, feel smooth and look shiny and lustrous when dry. The tresses shampooed with compositions A and B do not exhibit these characteristics.

We claim:
1. A powder shampoo concentrate comprising:
   (a) from about 50 to 75 parts by weight of an alkali metal or ammonium salt of an alpha olefin sulfonate having from 12 to 18 carbon atoms, and
   (b) from about 18 to 30 parts by weight of a nonionic hydroxypropyl polygalactomannan derivative with 0.35 to 0.60 moles of substitution.
2. The powder shampoo concentrate in accordance with claim 1 wherein component (a) is sodium alpha olefin sulfonate having from 14 to 16 carbon atoms.
3. The powder shampoo concentrate in accordance with claim 2 wherein component (b) is present in from about 20 to 25 parts by weight.
4. The powder shampoo concentrate in accordance with claim 3 comprising in addition from about 8 to 25 parts by weight of an alkali metal alkyl sulfate wherein the alkyl moiety has from 12–20 carbon atoms.
5. The powder shampoo concentrate in accordance with claim 4 wherein the alkali metal alkyl sulfate is sodium lauryl sulfate.
6. An aqueous shampoo composition useful for cleansing and conditioning hair comprising:
   I one part by weight of a powder shampoo concentrate comprising:
      (a) from about 50 to 75 parts by weight of an alkali metal of ammonium salt of an alpha olefin sulfonate having from 12 to 18 carbon atoms, and
      (b) from about 18 to 30 parts by weight of a nonionic hydroxypropyl polygalactomannan derivative with 0.35 to 0.60 moles of substitution.
   II from 38 to 40 parts by weight of water.
7. The shampoo composition of claim 6 wherein the powder concentrate comprises in addition from 8 to 25 parts by weight of an alkali metal alkyl sulfate, the alkyl moiety having from 12–20 carbon atoms.
8. A method for conditioning hair which comprises shampooing the hair with the composition of claim 6.

* * * * *